United States Patent
Ackerman et al.

(10) Patent No.: US 8,461,375 B2
(45) Date of Patent: Jun. 11, 2013

(54) METHOD FOR THE CONTINUOUS PRODUCTION OF ALKYL(METH)ACRYLATES WITH MULTIPLE CATALYST RECYCLING

(75) Inventors: Jochen Ackerman, Darmstadt (DE); Horst Hiltner, Heppenheim (DE); Hermann Siegert, Seeheim-Jugenheim (DE)

(73) Assignee: Evonik Röhm GmbH, Darmstadt (DE)

( * ) Notice: Subject to any disclaimer, the term of this patent is extended or adjusted under 35 U.S.C. 154(b) by 1451 days.

(21) Appl. No.: 10/541,307

(22) PCT Filed: Nov. 21, 2003

(86) PCT No.: PCT/EP03/13060
§ 371 (c)(1), (2), (4) Date: Apr. 10, 2006

(87) PCT Pub. No.: WO2004/063140
PCT Pub. Date: Jul. 29, 2004

(65) Prior Publication Data
US 2006/0211880 A1    Sep. 21, 2006

(30) Foreign Application Priority Data
Jan. 13, 2003 (DE) .................................. 103 01 007

(51) Int. Cl.
*C07C 67/03* (2006.01)

(52) U.S. Cl.
USPC ...................................................... 560/217

(58) Field of Classification Search
None
See application file for complete search history.

(56) References Cited

U.S. PATENT DOCUMENTS

| | | | |
|---|---|---|---|
| 3,386,576 A | 6/1968 | Falize et al. | |
| 5,734,074 A | 3/1998 | Dockner et al. | |
| 6,437,173 B1 | 8/2002 | Hurtel et al. | |
| 6,743,407 B2 | 6/2004 | Schaefer et al. | |
| 6,977,310 B2 * | 12/2005 | Ackermann et al. | 560/217 |
| 6,979,432 B2 | 12/2005 | Schaefer et al. | |
| 7,288,402 B2 | 10/2007 | Osswald et al. | |
| 7,491,521 B2 | 2/2009 | Osswald et al. | |
| 2004/0171868 A1 * | 9/2004 | Geisendoerfer et al. | 560/217 |
| 2005/0119500 A1 | 6/2005 | Ackermann et al. | |
| 2006/0211880 A1 | 9/2006 | Ackerman et al. | |
| 2007/0173664 A1 | 7/2007 | Krill et al. | |
| 2008/0248538 A1 | 10/2008 | Osswald et al. | |
| 2009/0118533 A1 | 5/2009 | Broell et al. | |

FOREIGN PATENT DOCUMENTS

| | | |
|---|---|---|
| DE | 23 19 688 | 12/1973 |
| DE | 100 00 171 | 7/2001 |
| DE | 100 26 644 | 12/2001 |
| DE | 101 27 939 | 5/2002 |
| EP | 0 733 617 A1 | 9/1996 |
| EP | 0 960 877 | 12/1999 |
| EP | 1 583 733 A1 | 10/2005 |
| FR | 2 777 561 A1 | 10/1999 |
| JP | 2006-513241 A | 4/2006 |
| WO | WO 01/92198 A1 | 12/2001 |

OTHER PUBLICATIONS

U.S. Appl. No. 11/915,042, filed Nov. 20, 2007, Ackermann et al.
U.S. Appl. No. 11/914,493, filed Nov. 15, 2007, Ackermann et al.
U.S. Appl. No. 11/995,206, filed Jan. 10, 2008, Sarcinelli et al.
U.S. Appl. No. 60/893,788, filed Mar. 8, 2007, May et al.
Office Action issued Aug. 31, 2010, in Canada Patent Application No. 2,512,628.
Office Action issued Nov. 21, 2003, in Brazilian Patent Application No. P10317983-4 with Informal English Translation.

\* cited by examiner

*Primary Examiner* — Yevegeny Valenrod
(74) *Attorney, Agent, or Firm* — Oblon, Spivak, McClelland, Maier & Neustadt, L.L.P.

(57) ABSTRACT

The invention relates to an improved method for the continuous production of alkyl(methyl)acrylates by transesterification of methyl(meth)acrylate with alcohols that are heavy in comparison with methanol. A special processing technique makes it possible to obtain new levels of product quality. Very high space-time-overall yields can also be obtained. The invention is characterized by the multiple use of a homogeneous catalyst which thereby reduces the costs of auxiliary agents significantly.

20 Claims, 5 Drawing Sheets

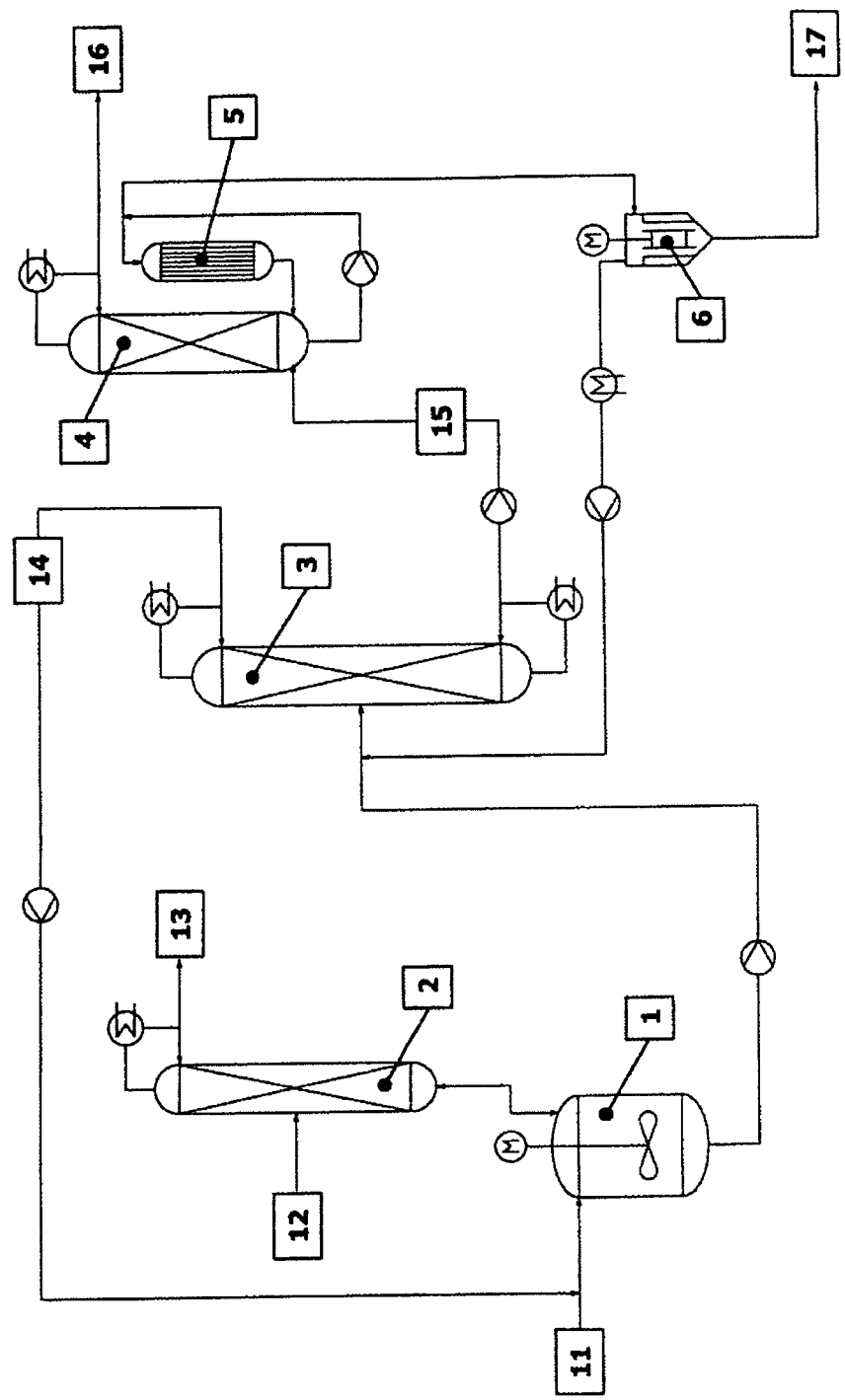
Figure 1: Prior Art

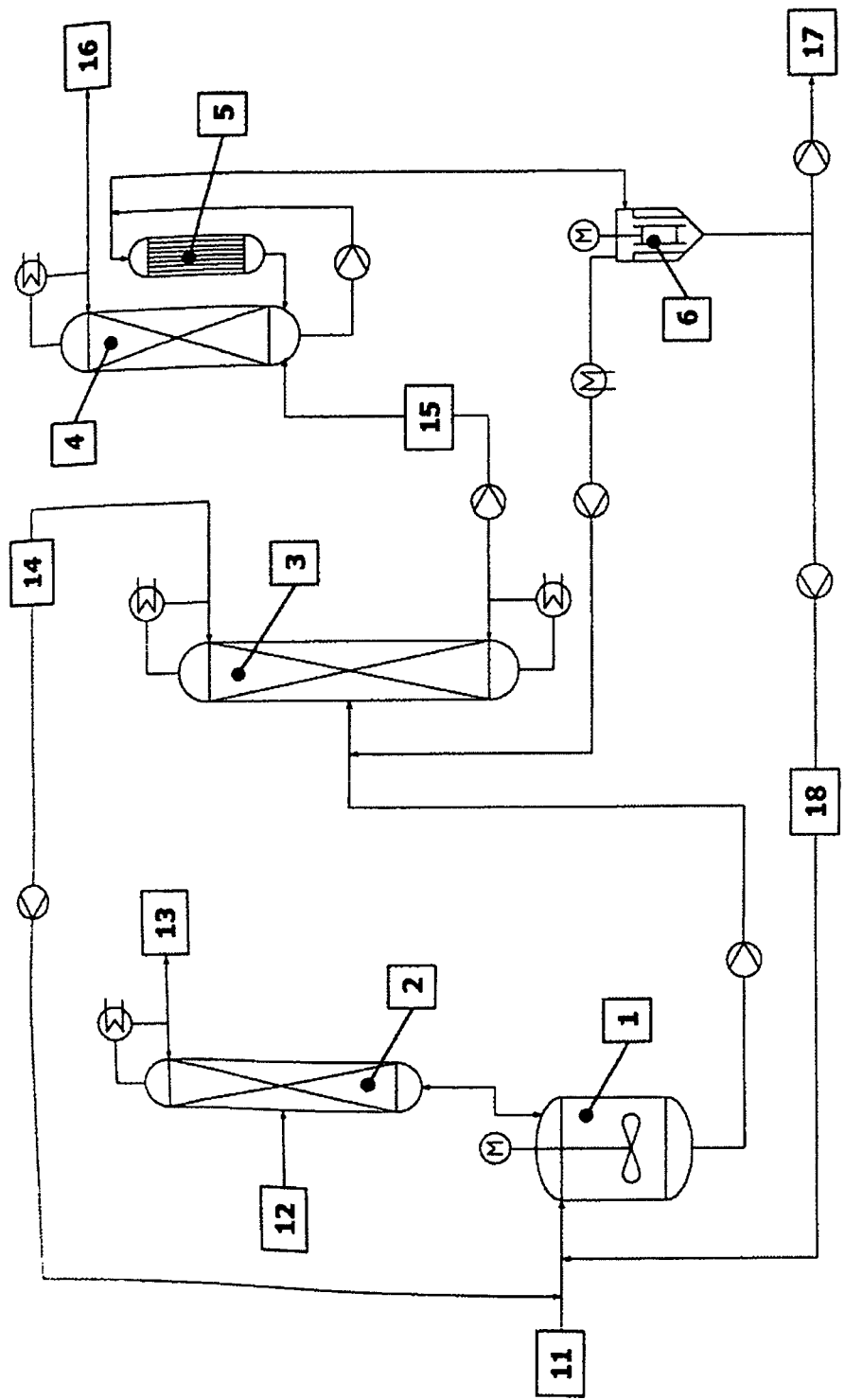
Figure 2: Solution variant 1

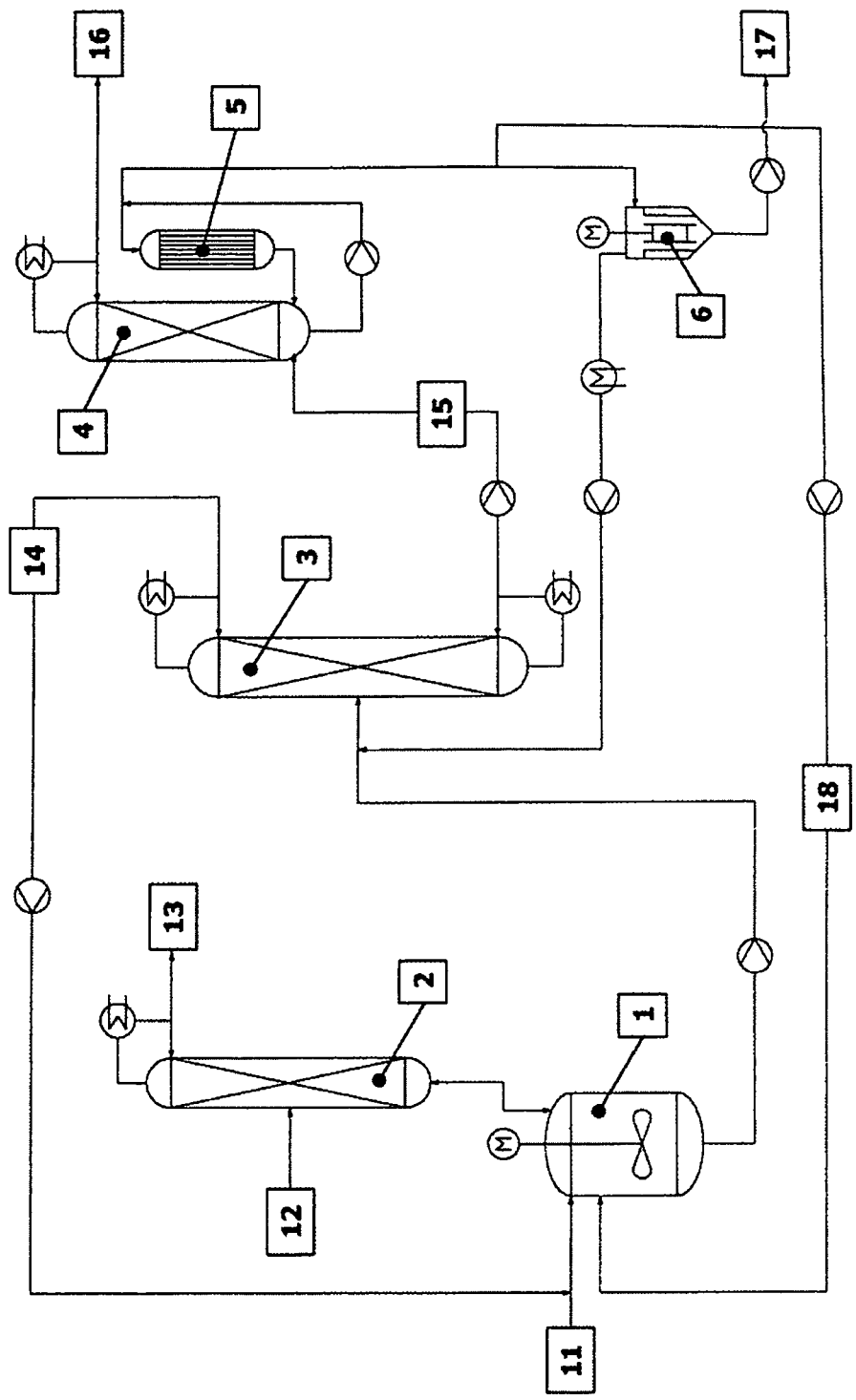
Figure 3: Solution variant 2

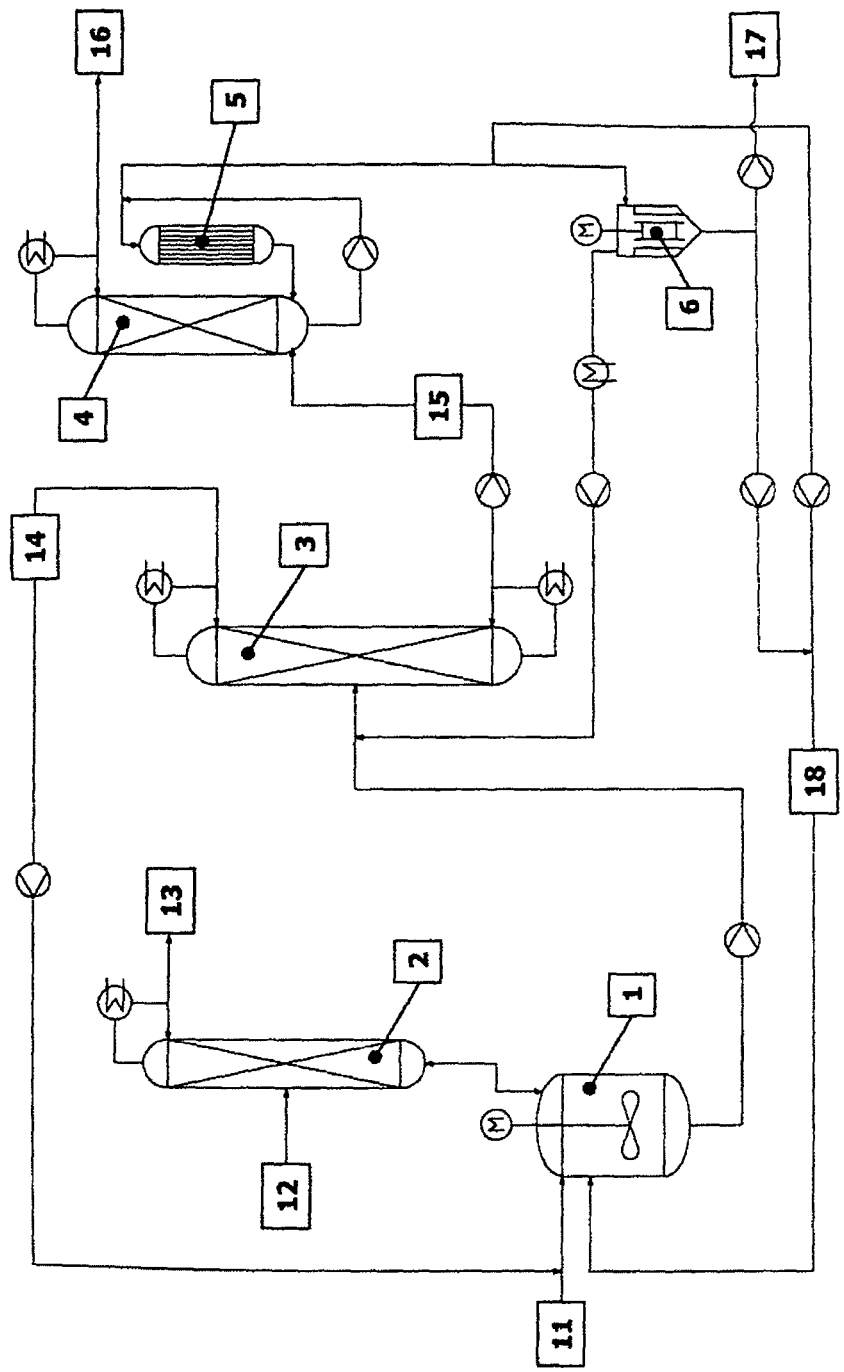
Figure 4: Solution variant 3

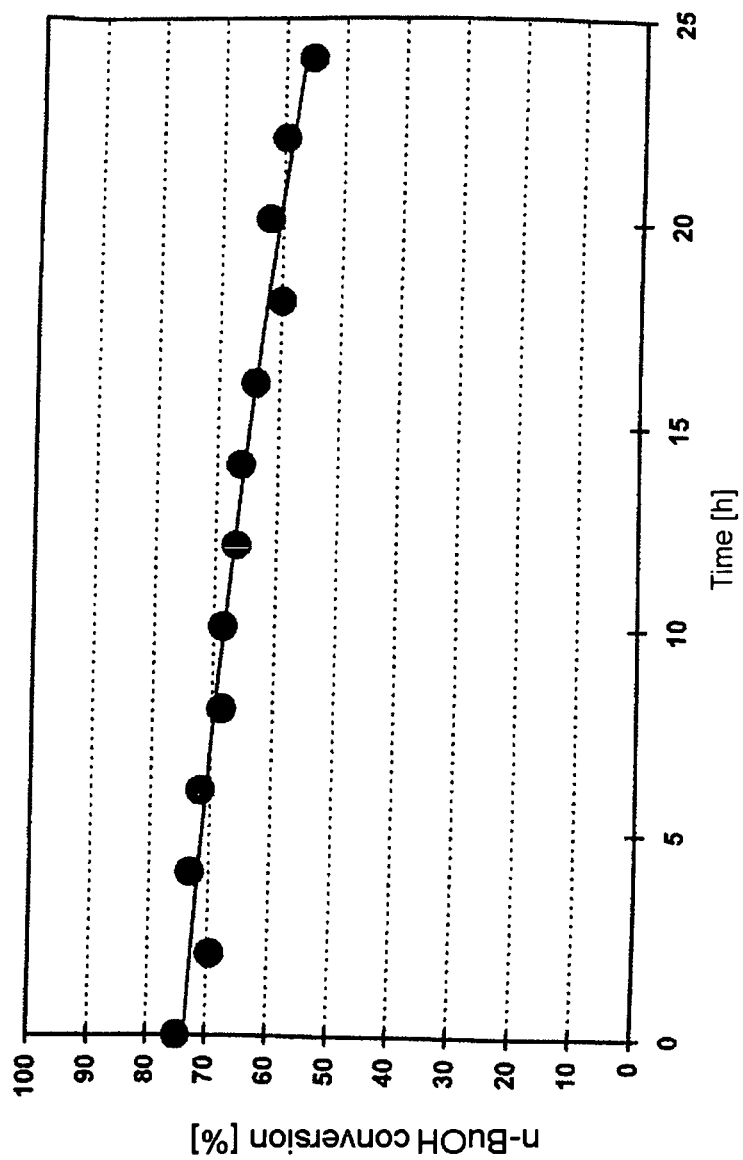
Figure 5: n-butanol (n-BuOH) conversion as a function of time with complete catalyst recycling

METHOD FOR THE CONTINUOUS PRODUCTION OF ALKYL(METH)ACRYLATES WITH MULTIPLE CATALYST RECYCLING

FIELD OF THE INVENTION

The present invention relates to a further improved continuous process for preparing alkyl(meth)acrylates (C) by continuously transesterifying methyl(meth)acrylate (A) with alcohols (B) to release methanol (D) according to the following reaction equation:

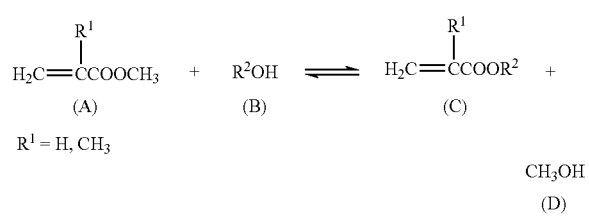

$R^1 = H, CH_3$ where $R^2$ is a linear, branched or cyclic alkyl radical or aryl radical having 2 to 12 carbon atoms. The $R^2$ group is, for example, the ethyl, n-propyl, isopropyl, allyl, n-butyl, 1-methylpropyl, 2-methylpropyl, tert-butyl, n-pentyl, 1-methylbutyl, 2-methylbutyl, 3-methylbutyl, 2,2-dimethylpropyl, n-hexyl, 1-methylpentyl, 2-methylpentyl, 3-methylpentyl, 4-methylpentyl, 1,1-dimethylbutyl, 2,2-dimethylbutyl, 3,3-dimethylbutyl, 1,2-dimethylbutyl, n-heptyl, 1-methylhexyl, 2-methylhexyl, 3-methylhexyl, 4-methylhexyl, 1,2-dimethylpentyl, 1,3-dimethylpentyl, 1,1-dimethylpentyl, 1,1,2,2-tetramethylpropyl, benzyl, n-octyl, 2-ethylhexyl, n-nonyl, 1-methyloctyl, 2-methyloctyl, n-decyl, n-undecyl, 1-methyldecyl, 2-methyldecyl, n-dodecyl, 2,4-diethyloctyl, cyclopentyl, cyclohexyl, 4-tert-butylcyclohexyl, cycloheptyl, cyclododecyl, 2-(dimethylamino)ethyl, 3-(dimethylamino)propyl, 4-(dimethylamino)butyl, 5-(dimethylamino)pentyl, 6-(dimethylamino)hexyl, 8-(dimethylamino)octyl, 10-(dimethylamino)decyl, 12-(dimethylamino)dodecyl, 2-(diethylamino)ethyl, 3-(diethylamino)propyl, 4-(diethylamino)butyl, 5-(diethylamino)pentyl, 6-(diethylamino)hexyl, 8-(diethylamino)octyl, 10-(diethylamino)decyl, 12-(diethylamino)dodecyl, 2-(di(isopropyl)amino)ethyl, 3-(di(isopropyl)amino)propyl, 4-(di(isopropyl)amino)butyl, 5-(di(isopropyl)amino)pentyl, 6-di(isopropyl)amino)hexyl, 8-(di(isopropyl)amino)octyl, 10-(di(isopropyl)amino)decyl, 12-(di(isopropyl)amino)dodecyl, 2-(dibutylamino)ethyl, 3-(dibutylamino)propyl, 4-(dibutylamino)butyl, 5-(dibutylamino)pentyl, 6-(dibutylamino)hexyl, 8-(dibutylamino)octyl, 10-(dibutylamino)decyl, 12-(dibutylamino)dodecyl, 2-(dihexylamino)ethyl, 3-(dihexylamino)propyl, 4-(dihexylamino)butyl, 5-(dihexylamino)pentyl, 6-(dihexylamino)hexyl, 8-(dihexylamino)octyl, 10-(dihexylamino)decyl, 12-(dihexylamino)dodecyl, 2-(methylethylamino)ethyl, 2-(methylpropylamino)ethyl, 2-(methylisopropylamino)ethyl, 2-(methylbutylamino)ethyl, 2-(methylhexylamino)ethyl, 2-(methyloctylamino)ethyl, 2-(ethylpropylamino)ethyl, 2-(ethylisopropylamino)ethyl, 2-(ethylbutylamino)ethyl, 2-(ethylhexylamino)ethyl, 2-(ethyloctylamino)ethyl, 3-(methylethylamino)propyl, 3-(methylpropylamino)propyl, 3-(methylisopropylamino)propyl, 3-(methylbutylamino)propyl, 3-(methylhexylamino)propyl, 3-(methyloctylamino)propyl, 3-(ethylpropylamino)propyl, 3-(ethylisopropylamino)propyl, 3-(ethylbutylamino)propyl, 3-(ethylhexylamino)propyl, 3-(ethyloctylamino)propyl, 4-(methylethylamino)butyl, 4-(methylpropylamino)butyl, 4-(methylisopropylamino)butyl, 4-(methylbutylamino)butyl, 4-(methylhexylamino)butyl, 4-(methyloctylamino)butyl, 4-(ethylpropylamino)butyl, 4-(ethylisopropylamino)butyl, 4-(ethylbutylamino)butyl, 4-(ethylhexylamino)butyl, 4-(ethyloctylamino)butyl, 2-(N-piperidinyl)ethyl, 3-(N-piperidinyl)propyl, 4-(N-piperidinyl)butyl, 5-(N-piperidinyl)pentyl, 6-(N-piperidinyl)hexyl, 8-(N-piperidinyl)octyl, 10-(N-piperidinyl)decyl, 12-(N-piperidinyl)dodecyl, 2-(N-pyrrolidinyl)ethyl, 3-(N-pyrrolidinyl)propyl, 4-(N-pyrrolidinyl)butyl, 5-(N-pyrrolidinyl)pentyl, 6-(N-pyrrolidinyl)hexyl, 8-(N-pyrrolidinyl)octyl, 10-(N-pyrrolidinyl)decyl, 12-(N-pyrrolidinyl)dodecyl, 2-(N-morpholino)ethyl, 3-(N-morpholino)propyl, 4-(N-morpholino)butyl, 5-(N-morpholino)pentyl, 6-(N-morpholino)hexyl, 8-(N-morpholino)octyl, 10-(N-morpholino)decyl, 12-(N-morpholino)dodecyl, 2-(N-methyl-N-piperazinyl)ethyl, 3-(N'-methyl-N-piperazinyl)propyl, 4-(N'-methyl-N-piperazinyl)butyl, 5-(N'-methyl-N-piperazinyl)pentyl, 6-(N'-methyl-N-piperazinyl)hexyl, 8-(N'-methyl-N-piperazinyl)octyl, 10-(N'-methyl-N-piperazinyl)decyl, 12-(N'-methyl-N-piperazinyl)dodecyl, 2-(N'-ethyl-N-piperazinyl)ethyl, 3-(N'-ethyl-N-piperazinyl)propyl, 4-(N'-ethyl-N-piperazinyl)butyl, 5-(N'-ethyl-N-piperazinyl)pentyl, 6-(N'-ethyl-N-piperazinyl)hexyl, 8-(N'-ethyl-N-piperazinyl)octyl, 10-(N'-ethyl-N-piperazinyl)decyl, 12-(N'-ethyl-N-piperazinyl)dodecyl, 2-(N'-isopropyl-N-piperazinyl)ethyl, 3-(N'-isopropyl-N-piperazinyl)-propyl, 4-(N'-isopropyl-N-piperazinyl)butyl, 5-(N'-isopropyl-N-piperazinyl)pentyl, 6-(N'-isopropyl-N-piperazinyl)hexyl, 8-(N'-isopropyl-N-piperazinyl)octyl, 10-(N'-isopropyl-N-piperazinyl)decyl, 12-(N'-isopropyl-N-piperazinyl)dodecyl, 3-oxabutyl, 3-oxapentyl, 2,2-dimethyl-4-oxapentyl, 3,6-dioxaheptyl, 3,6-dioxaoctyl, 3,6,9-trioxadecyl, 3,6,9-trioxaundecyl, 4-oxapentyl, 4-oxahexyl, 4-oxaheptyl, 4,8-dioxanonyl, 4,8-dioxadecyl, 4,8-dioxaundecyl, 5-oxahexyl, or the 5,10-dioxaundecyl group.

$R^2OH$ may also be ethoxylated and/or propoxylated alcohols, and also mixed ethoxylated/propoxylated alcohols such as $R^5-(O-CH_2-CH_2)_x-OH$ or $R^5-(O-CH(CH_3)-CH_2)_x-OH$ or $R^5-(O-CH_2-CH(CH_3))_x-OH$ where $R^5$ is $C_1$ to $C_{20}$-alkyl and x is an integer in the range from 10 to 20, or ethoxylated and/or propoxylated amino alcohols $R^3{}_2N(-CH_2-CH_2-O)_y-H$ or $R^3{}_2N(-CH(CH_3)-CH_2-O)_y-H$ or $R^3{}_2N(-CH_2CH(CH_3)-O)_y-H$, where y is an integer in the range from 1 to 4.

$R^3$ is an alkyl group having 1-6 carbon atoms, and the nitrogen atom may also form a five- to seven-membered ring with the $R^3$ substituents. The ring may optionally also be substituted by one or more short-chain alkyl groups, for example methyl, ethyl or propyl.

In the process according to the invention, preference is given to using n-butanol, isobutanol and 2-ethylhexanol.

The improvement over the prior art is that the homogeneous tetraalkyl titanate (tetraalkoxytitanium) catalyst which is used with preference can surprisingly be used repeatedly by recycling. This decisively reduces the catalyst consumption and consequently the costs of the auxiliaries, which again distinctly increases the economic viability of the process.

PRIOR ART

Alkyl(meth)acrylates can be prepared continuously in various methods by transesterifying methyl(meth)acrylate in the presence of catalysts.

EP 0 960 877 (Elf Atochem S. A.) describes a continuous process for preparing methacrylate esters of dialkylamino alcohols. Dialkylamino alcohols are generally reacted with methyl(meth)acrylate to obtain the dialkylaminoalkyl(meth)acrylate by the following process:

The mixture of starting materials (methyl(meth)acrylate and dialkylamino alcohol) is continuously fed to a stirred reactor together with a homogeneous tetraalkyl titanate transesterification catalyst (for example tetrabutyl titanate, tetraethyl titanate or tetra(2-ethylhexyl) titanate) and at least one polymerization inhibitor (for example phenothiazine, tert-butylcatechol, hydroquinone monomethyl ether or hydroquinone), and the conversion to the dialkylamino(meth)acrylate is effected in the stirred reactor at a temperature of 90-120° C. while continuously removing the azeotropic methyl(meth)acrylate/methanol mixture. The crude reaction mixture (crude ester) is fed to a first distillation column in which, under reduced pressure, a substantially catalyst-free stream is withdrawn overhead, and the catalyst and also a little dialkylaminoalkyl(meth)acrylate are removed at the bottom of the distillation column. The top stream of the first distillation column is then fed to a second distillation column in which, under reduced pressure, a stream of low-boiling products comprising a little dialkylaminoalkyl(meth)acrylate is withdrawn overhead and a stream consisting mainly of dialkylaminoalkyl(meth)acrylate and also polymerization inhibitor(s) is removed at the bottom and is fed to a third distillation column. In the third distillation column, a rectification is carried out under reduced pressure in which the desired pure dialkylaminoalkyl(meth)acrylate ester is withdrawn overhead and essentially the polymerization inhibitor or the polymerization inhibitors are withdrawn at the bottom. After further purification with the aid of a film evaporator, the bottom stream of the first distillation column is recycled into the reactor, like the top stream from the second distillation column.

A detailed description of the procedure for recycling the homogeneous catalyst is not specified. It can merely be discerned from the specified purification of the bottom effluent of the first distillation column using a film evaporator that the remaining dialkylaminoalkyl(meth)acrylate is removed from the catalyst and also high-boiling secondary components, and recycled into the reactor.

EP 0 968 995 (Mitsubishi Gas Chemical Comp.) describes a continuous process for preparing alkyl(meth)acrylic esters using a reaction column. The transesterification is effected directly within a distillation column (i.e. reactor and distillation column for removing the methyl(meth)acrylate/methanol azeotrope form one apparatus), into which the starting materials (methyl(meth)acrylate and alcohol) are fed continuously. The necessary catalyst, here likewise preferably a titanium compound, is in the distillation column. In the case of a homogeneous catalyst, the catalyst is continuously metered into the distillation column. However, owing to the flushing effect of the liquid reflux in a distillation column, the use of homogeneous catalysts in the distillation column leads to an increased catalyst requirement and also, when a solid catalyst precipitate occurs, to fouling of the column internals. In the case of a heterogeneous catalyst, the catalyst is in the reaction column. However, the positioning of the catalyst in the distillation column is disadvantageous because an increased pressure drop then occurs in the distillation column and very high additional cost and inconvenience are associated with regular cleaning of the distillation column. Also, heterogeneous catalysts may deactivate, for example as a consequence of undesired polymerization.

No information is given on the procedure for recycling a homogeneous catalyst into the reaction column after removing crude ester beforehand.

Compared to the aforementioned processes, the German patent application no. 102 00 171.5 describes a distinctly improved continuous process for preparing alkyl(meth)acrylates by transesterifying methyl(meth)acrylate with alcohols having a higher boiling point than methanol (cf. FIG. 1).

The reactants methyl(meth)acrylate (MMA, 11) and alcohol (12) are fed continuously to a suitable reaction apparatus (1) which may be either a single reaction tank or else a battery of two or more reaction tanks connected in series. It is sensible that all reaction tanks should have a vapour takeoff to the azeotrope distillation column (2) for removing the methanol released in the reaction. The homogeneous tetraalkyl titanate catalyst which is used with preference (the tetraalkoxytitanium content relative to MMA used is preferably 0.2-0.5% by weight) is metered continuously into the reaction apparatus (1), as is/are the polymerization inhibitor(s). However, the transesterification catalysts used may also be any transesterification catalysts disclosed by the prior art. Examples of polymerization inhibitors include hydroquinone monomethyl ether in combination with oxygen. Since the alcohol used may contain water (the amount of water in the alcohol used in the case of n-butanol is between 0.05-0.005% by weight), preference is given to distillatively dewatering the alcohol using the azeotrope column (2) before entry into the reaction apparatus. The water contained in the alcohol is removed overhead. To avoid contamination of the methanol/MMA azeotrope (13) with the alcohol used, the alcohol is preferably added in the lower section of the distillation column (2). However, the alcohol used may also be dewatered by using an upstream dewatering distillation column, by treating with a dewatering agent, for example a molecular sieve, or by a membrane separating process, for example a pervaporation. The dewatering is significant because the water contained in the alcohol can lead to irreversible damage of the catalyst (for example tetraalkyl titanate) in the reactor. This dewatering step avoids the hydrolysis of the catalyst and the costs resulting from increased catalyst use quantities and from problems with solid precipitates. The reaction is effected in the reaction apparatus at a temperature in the range of 80 to 160° C. Preference is given to the temperature range of 110 to 135° C. To positively influence the reaction equilibrium, the methanol released in the reaction is removed from the reaction mixture as an azeotrope with MMA (13) using the distillation column (2). The reaction mixture which consists predominantly of the product alkyl(meth)acrylate, unconverted MMA and alcohol and also small amounts of methanol, the catalyst, the polymerization inhibitors and a very low proportion of by-products is fed to a continuously operated low boiler distillation column (3) after about 0.5-3 hours of reactor residence time (preference is given to a residence time of 0.75-1.5 hours). Components which are low-boiling relative to the product ester, predominantly methanol, MMA and unconverted reactant alcohol, are removed there under reduced pressure, preferably in the range of 20-200 mbar. These components are removed overhead in the distillation column and recycled into the reactor region (14). This cycle stream guarantees that, based on the overall process, there is virtually complete conversion with regard to the reactants MMA and alcohol. The crude ester (15) which is obtained at the bottom of the distillation column (3) and is still contaminated with catalyst, polymerization inhibitor and high-boiling by-products preferably comprises >98% by weight of product ester and is fed continuously for workup to a further vacuum distillation stage (4, 5) which operates in the preferred pressure range of 20 to 200 mbar. The highly pure product ester is continuously distillatively removed here as the top product (16). When a conventional vacuum distillation column as described in the prior art is used for removing the catalyst and the polymerization inhibitors and also the high-boiling by-products from the crude ester (15), impermissibly high thermal stress in the bottom of the column results in decomposition of the catalyst and therefore release of the reactant alcohol and sometimes also the formation of ethers of the reactant alcohol. Both compounds (reactant alcohol and ether of the reactant alcohol) are low-boiling components with respect to the product ester and therefore occur as an impurity in the product ester, which distinctly reduces the product quality. This problem may be solved by using an apparatus having gentle film evaporation (5) to remove the product ester from the catalyst and the polymerization inhibitors and also the high-boiling by-products. Useful apparatus for this purpose include falling-film, thin-film and short-path evaporators. A further downstream high boiler distillation stage (4) serves to achieve the highest product ester purity (product ester>99.9% by weight, alcohol<120 ppm, MMA<10 ppm, ether<5 ppm, colour number (apha)<1). In this context, however, a single apparatus employing film evaporation has the disadvantage of offering insufficient purifying performance so that high-boiling by-products also occur in the pure product ester (16). This problem is solved by positioning a vacuum rectification column (4) for removing the high-boiling by-products from the pure product ester above the apparatus employing film evaporation. After removing the catalyst and the polymerization inhibitors and also the high-boiling by-products from the crude ester, a certain proportion of product ester remains in the bottom product, so that the bottom effluent is still able to flow and be conveyed efficiently. In order to minimize the loss of product ester when discharging catalyst, polymerization inhibitors and high-boiling by-products (17), there should be a downstream vacuum evaporation stage (6) which operates in the preferred pressure range of 20-200 mbar. A useful apparatus for this task is again an apparatus employing film evaporation. Useful apparatus for this purpose again includes falling-film, thin-film and short-path evaporators. Owing to an excessive content of high-boiling components, the product ester removed overhead in the evaporation stage does not fulfil the required specification for the pure product ester. Furthermore, owing to the thermal decomposition of the catalyst, it also contains reactant alcohol and sometimes also ethers of the reactant alcohol. For these reasons, the aim of recovering the product ester from the distillate stream cannot be achieved by recycling it directly into the high boiler distillation column (4), but rather by recycling to the reaction apparatus (1) or advantageously to the low boiler distillation column (3) in order to remove the low boilers before the first evaporation stage (5).

The process has the disadvantage that the partly inactive, homogeneous catalyst which has been repeatedly thermally stressed and is therefore possibly damaged, after it has been removed from the product ester, is discharged in its entirety with the polymerization inhibitors and high-boiling by-products and is not reused by recycling. As a consequence of the relatively high catalyst cost, this leads to increased costs of auxiliaries.

DE 101 27 939 (BASF) describes a continuous transesterification process. The formulation of one of the partial objects to be achieved is that the catalyst should be reusable without any problem.

It is an object of the present invention to provide a process which is free of said weaknesses and fulfills the following criteria:

1. The starting materials (catalyst, stabilizer, lower (meth)acrylate) should be economical, easy to handle and available in industrial quantity.
2. The catalyst should be stable at elevated temperatures and in the presence of small amounts of water.
3. The loss of activity of the catalyst should be small and said catalyst should be capable of being reused without problems.
4. No alcohol foreign to the system should be introduced into the transesterification via the transesterification catalyst.
5. Long times-on-stream of the plant, i.e. very few polymerization problems and use of apparatuses which require very little repair.
6. Direct reuse or utilization of the resulting mixture or azeotropic mixture of lower alkanol and the corresponding ester.
7. Substantial recovery of the remaining useful products from the waste streams and from the by-products.
8. The transesterification should preferably be operated continuously.
9. The desired ester should have a high purity (at least 99.9%) and, in the case of the preparation of the dialkylaminomethyl(meth)acrylates, the formation of ethylene glycol di(meth)acrylate and vinyloxyethyl(meth)acrylate should be reduced, as far as possible, to below 100 ppm.
10. The amounts of waste should be very small and easy to handle.
11. Conversion and yield should be high (>95%).
12. The residence times should be short.
13. The overall process should be technically simple and economical.

Although this object is formulated, there are no indications in the description of selective recycling of the active or semi-active catalyst. Further, there is no information on the numerical ratios in the recycling of the catalyst or information on any changes in the product quality when a fully or partly recycled transesterification catalyst is used.

OBJECT

It is an object of the present invention to provide a continuous process for transesterifying methyl(meth)acrylate (A) with alcohols (B) having a higher boiling point than methanol (D), in which the homogeneous catalyst used can be used repeatedly by partial recycling. In this context, (meth)acrylic esters or alkyl(meth)acrylates refer hereinbelow to esters and derivatives of acrylic acid and of methacrylic acid. In addition, the novel process should provide a product whose quality is better than that of those already on the market. The novel process should further allow alkyl(meth)acrylates to be prepared in a very uncomplicated and energetically more efficient manner using a smaller amount of auxiliary (i.e. more cost-effectively). This object, and also further objects which are not specifically illustrated in more detail but which can be inferred or derived without further information from the introductory discussion of the prior art, are achieved by a process as illustrated hereinbelow.

SOLUTION

Starting from the prior art established by Röhm (DE 102 00 171.5), it has been found that, surprisingly, the homogeneous tetraalkyl titanate (tetraalkoxytitanium) catalyst which is used with preference still has considerable activity at various points in the process despite thermal stress in the column bottoms and film evaporators. Repeated use of the catalyst over and above simple run-through is therefore possible. This allows the costs of auxiliaries to be distinctly reduced with unchanged product qualities and unchanged space-time and overall yields. For this purpose, all that is additionally required is a liquid stream divider and a pump. The amount of catalyst which is recycled is controlled with the aid of alcohol (B) or MMA (A) conversion in the reaction apparatus (1) as a measure of the current catalyst activity. A further indicator which can be used for the current catalyst activity is the amount and composition of the low boiler cycle stream (14). For the industrial implementation of the catalyst recycling, the following solution variants are possible in principle:

Solution Variant 1 (FIG. 2):

The bottom effluent of the vacuum evaporation stage (6) which comprises the catalyst, polymerization inhibitors, and also high-boiling by-products and residual product ester is divided and recycled partly (18) to the reaction apparatus (1). The remaining residual stream is discharged (17). The discharge (17) is in proportion to the steady-state amount of high-boiling secondary components which has been formed and in proportion to the remaining residual activity of the catalyst in the bottom effluent of the vacuum evaporation stage (6). The fresh amount of catalyst in the stream (11) is reduced in proportion to the recycled amount of catalyst compared to the operation without catalyst recycling.

The recycled stream (18) is between 1 and 95% by weight, preferably between 40 and 90% by weight and most preferably between 60 and 85% by weight, of the bottom effluent from the vacuum evaporation stage (6).

Solution Variant 2 (FIG. 3):

The bottom effluent from the apparatus employing gentle film evaporation (5) which remains after the highly pure product ester has been removed and comprises the catalyst, polymerization inhibitors and also high-boiling by-products and residual product ester is divided and recycled in part (18) into the reaction apparatus (1). The remaining residual stream is fed to a vacuum evaporation stage (6) in accordance with the prior art, where the majority of the product ester is removed and recycled to the reaction apparatus (1) or advantageously to the low boiler distillation column (3). The bottom effluent of the vacuum evaporation stage (6) which comprises the catalyst, polymerization inhibitors and also high-boiling by-products and residual product ester is discharged (17). The discharge (17) is in proportion to the steady-state amount of high-boiling secondary components which has been formed and is in proportion to the remaining residual activity of the catalyst in the bottom effluent of the vacuum distillation stage (4, 5). The fresh amount of catalyst in stream (11) is reduced in proportion to the amount of catalyst which is recycled compared to the operation without catalyst recycling.

The recycle stream (18) is between 1 and 95% by weight, preferably between 40 and 90% by weight and most preferably between 60 and 85% by weight, of the bottom effluent from the film evaporator (5).

Solution Variant 3 (FIG. 4):

The bottom effluent from the apparatus employing gentle film evaporation (5) which remains after the highly pure product ester has been removed and comprises the catalyst, polymerization inhibitors and also high-boiling by-products and residual product ester is divided and recycled in part (18) into the reaction apparatus (1). The remaining residual stream is fed to a vacuum evaporation stage (6) in accordance with the prior art, where the majority of the product ester is removed and recycled to the reaction apparatus (1) or advantageously to the low boiler distillation column (3). The bottom effluent of the vacuum evaporation stage (6) which comprises the catalyst, polymerization inhibitors and also high-boiling by-products and residual product ester is divided and likewise partly recycled (18) into the reaction apparatus (1). The remaining residual stream is discharged (17). The discharge (17) is proportional to the steady-state amount of high-boiling secondary components which has been formed and proportional to the remaining residual activity of the catalyst in the recycle stream (18). The fresh amount of catalyst in stream (11) is reduced in proportion to the recycled amount of catalyst compared to the operation without catalyst recycling.

The recycle stream (18) is between 1 and 95% by weight, preferably between 40 and 90% % by weight and most preferably between 60 and 85% by weight, of the sum of the bottom effluents from the film evaporator (5) and from the vacuum evaporation stage (6).

EXAMPLES

The process according to the invention is illustrated in detail by the examples which follow, without being restricted to them.

The examples cited were carried out in an experimental plant on the pilot scale (throughput per hour: 6-8 kg of feed (MMA and alcohol) and 5-6 kg of product ester). The construction of the experimental plant was as illustrated in FIG. 3 or in slightly modified form.

Comparative Example 1

No Recycling of the Catalyst (n-/i-butyl methacrylate Preparation)

The reaction apparatus (1) used was a steam-heated stainless steel reaction tank having a maximum fill volume of 15 l. The reactor was connected via a vapour line to an azeotrope distillation column (2) mounted above. The azeotrope distillation column (top pressure=1 $bar_{abs}$) was a pilot plant glass column having a diameter D=0.1 m and packed with Sulzer CY structured metal gauze packings of H=2 m. The feed for the reactant alcohol was disposed in the middle of the column (H=1 m). The reactor effluent was fed continuously to a low boiler distillation column (3). This distillation column was a pilot plant vacuum glass column (top pressure=120 $mbar_{abs}$) having a diameter D=0.1 m and packed with Sulzer CY structured metal gauze packings of H=3.8 m. The feed was at H=2 m. The bottom was heated by means of steam. The condensed top takeoff (cycle stream) (14) was recycled continuously to the reactor. Instead of the falling-film evaporator (5) shown in FIG. 3, the continuous workup of the bottom effluent of the low boiler distillation column (15) was carried out using a thermal oil-heated glass thin-film evaporator having an evaporator surface area A=0.1 m². The vapours of this glass thin-film evaporator were passed continuously into a high boiler distillation column (4) mounted above. This was a pilot plant vacuum glass column (top pressure=120 $mbar_{abs}$) having a diameter D=0.05 m and packed with Sulzer EX structured metal gauze packings of H=0.5 m. The bottom effluent was fed continuously to a second, smaller, likewise thermal oil-heated glass thin-film evaporator (6) (top pressure=120 $mbar_{abs}$) having an evaporator surface area A=0.02 m². The vapours of this second glass thin-film evaporator were condensed out and, combined with the reactor effluent, fed continuously to the low boiler distillation column. The bottom effluent (17) was continuously discharged from the process. The reactants (MMA and alcohol) were metered in continuously by means of piston metering pumps, and the catalyst (tetraalkyl titanate) was metered in dissolved in (water-free as per the specification) MMA feed. The MMA/catalyst feed was fed directly to the reactor, and the alcohol feed introduced preheated (to the internal column temperature) to the middle of the azeotrope distillation column. The continuous addition of 50-100 g/h of stabilizer solution (0.2% by weight of hydroquinone monomethyl ether in MMA or product ester) into the reflux stream of the distillation columns was effected with the aid of hose pumps. The continuous conveyance of the streams between the parts of the plant was effected either with the aid of piston metering pumps or by the sucking effect of the vacuum. Intermediate vessels (buffer volumes) were avoided as far as possible. The composition of the streams (MMA, alcohol, MeOH and product ester content) was determined with the aid of a gas chromatograph.

To continuously prepare n-butyl methacrylate (n-BuMA), 4 kg/h of MMA feed, 18 g/h of tetra-n-butyl titanate (Ti(n-OBu)$_4$) and 2.7 kg/h of n-BuOH feed were metered into the reaction tank (11). The recycle stream from the top of the low boiler distillation column also flowed continuously into the reactor (2.8 kg/h having the following composition: 1.0% by weight of n-BuMA, 38.3% by weight of n-BuOH, 57.3% by weight of MMA and 3.4% by weight of MeOH). The molar MMA:n-BuOH ratio in the reactor feed was 1.1:1. At a reactor residence time of 1 h and an MMA/MeOH azeotrope takeoff of 1.5 kg/h, a reactor temperature of 115° C. was attained. The composition of the MMA/MeOH azeotrope was 82% by weight of MeOH, 18% by weight of MMA and <5 ppm of n-BuOH. The resulting reactor effluent of 8 kg/h had the following composition: 64.6% by weight of n-BuMA, 13.5% by weight of n-BuOH, 20.3% by weight of MMA, 1.3% by weight of MeOH and 0.3% by weight of by-products. The space-time yield of the reactor based on n-BuMA was therefore 570 kg/h/m$^3$. Owing to virtually complete removal of low-boiling components relative to n-BuMA, the bottom effluent of the low boiler distillation column was a crude ester (5.8 kg/h) which already contained >99.5% by weight of n-BuMA and also all of the catalyst and the stabilizer. The yield of n-BuOH based on the overall process was therefore virtually 100%. The yield of MMA based on the overall process minus the MMA loss via the MMA/MeOH azeotrope calculated beforehand was likewise virtually 100%. At an evaporation ratio (ratio of vapour stream to feed stream) in the first, larger thin-film evaporator of about 90%, 5.1 kg/h of pure n-BuMA are finally obtained at the top of the high boiler distillation column and have the following composition: >99.92% by weight of n-BuMA, <120 ppm of n-BuOH, <10 ppm of MMA, <5 ppm of di-n-butyl ether, colour number (apha)<0.2. At an evaporation ratio in the second, smaller thin-film evaporator of about 90%, the overall discharge of the process (catalyst, stabilizer, high-boiling by-products, n-BuMA) is 0.1 kg/h and the yield loss of n-BuMA based on the pure n-BuMA produced is <0.5% by weight.

The catalyst consumption is 3.5 g of tetra-n-butyl titanate/kg of pure n-BuMA.

To continuously prepare isobutyl methacrylate (i-BuMA), 3.4 kg/h of MMA feed, 19 g/h of tetra-1-butyl titanate (Ti(i-OBu)$_4$) and 2.36 kg/h of i-BuOH feed were metered into the reaction tank. The recycle stream from the top of the low boiler distillation column also flowed continuously into the reactor (2.4 kg/h having the following composition: 6.2% by weight of i-BuMA, 35.3% by weight of i-BuOH, 56.3% by weight of MMA and 2.2% by weight of MeOH). The molar MMA:i-BuOH ratio in the reactor feed was 1.1:1. At a reactor residence time of 1.2 h and an MMA/MeOH azeotrope takeoff of 1.26 kg/h, a reactor temperature of 115° C. was attained. The composition of the MMA/MeOH azeotrope was 82% by weight of MeOH, 18% by weight of MMA and <5 ppm of i-BuOH.

The resulting reactor effluent of 6.9 kg/h had the following composition: 67.3% by weight of i-BuMA, 12.0% by weight of i-BuOH, 19.4% by weight of MMA, 0.8% by weight of MeOH and 0.5% by weight of by-products. The space-time yield of the reactor based on i-BuMA was therefore 516 kg/h/m$^3$. Owing to virtually complete removal of low-boiling components relative to i-BuMA, the bottom effluent of the low boiler distillation column was a crude ester (5.0 kg/h) which already contained >99.5% by weight of i-BuMA and also all of the catalyst and the stabilizer. The yield of i-BuOH based on the overall process was therefore virtually 100%. The yield of MMA based on the overall process minus the MMA loss via the MMA/MeOH azeotrope calculated beforehand was likewise virtually 100%. At an evaporation ratio (ratio of vapour stream to feed stream) in the first, larger thin-film evaporator of about 90%, 4.5 kg/h of pure i-BuMA are finally obtained at the top of the high boiler distillation column and have the following composition: >99.9% by weight of i-BuMA, <150 ppm of i-BuOH, <10 ppm of MMA, 0 ppm of di-1-butyl ether, colour number (apha)<0.2. At an evaporation ratio in the second, smaller thin-film evaporator of about 90%, the overall discharge of the process (catalyst, stabilizer, high-boiling by-products, i-BuMA) is 0.05 kg/h and the yield loss of i-BuMA based on the pure i-BuMA produced is <0.5% by weight.

The catalyst consumption is 4.2 g of tetra-1-butyl titanate/kg of pure i-BuMA.

Example 2

Complete Recycling of the Catalyst (n-Butyl Methacrylate Preparation)

The reaction apparatus (1) used was a steam-heated stainless steel reaction tank having a maximum fill volume of 15 l. The reactor was connected via a vapour line to an azeotrope distillation column (2) mounted above. The azeotrope distillation column (top pressure=1 bar$_{abs}$) was a pilot plant glass column having a diameter D=0.1 m and packed with Sulzer CY structured metal gauze packings of H=2 m. The feed for the reactant alcohol was disposed in the middle of the column (H=1 m). The reactor effluent was fed continuously to a low boiler distillation column (3). This distillation column was a pilot plant vacuum glass column (top pressure=120 mbar$_{abs}$) having a diameter D=0.1 m and packed with Sulzer CY structured metal gauze packings of H=3.8 m. The feed was at H=2 m. The bottom was heated by means of steam. The condensed top takeoff (cycle stream) (14) was recycled continuously to the reactor. Instead of the falling-film evaporator (5) shown in FIG. 3, the continuous workup of the bottom effluent of the low boiler distillation column (15) was carried out using a thermal oil-heated glass thin-film evaporator having an evaporator surface area A=0.1 m$^2$. The vapours of this glass thin-film evaporator were passed continuously into a high boiler distillation column (4) mounted above. This was a pilot plant vacuum glass column (top pressure=150 mbar$_{abs}$) having a diameter D=0.05 m and packed with Sulzer EX structured metal gauze packings of H=0.5 m. The bottom effluent was continuously recycled into the reaction tank (18) and also partly discharged continuously from the process (17). At time t=0 h, the bottom effluent was recycled fully and continuously into the reaction tank (18) and there was no longer any discharge (17) nor fresh catalyst metering. The reactants (MMA and alcohol) were metered in continuously by means of piston metering pumps, and the catalyst (tetraalkyl titanate) was metered in dissolved in (water-free as per the specification) MMA feed. The MMA/catalyst feed was fed directly to the reactor, and the alcohol feed introduced preheated (to the internal column temperature) to the middle of the azeotrope distillation column. The continuous addition of 50-100 g/h of stabilizer solution (0.2% by weight of hydroquinone monomethyl ether in MMA or product ester) into the reflux stream of the distillation columns was effected with the aid of hose pumps. The continuous conveyance of the streams between the parts of the plant was effected either with the aid of piston metering pumps or by the sucking effect of the vacuum. Intermediate vessels (buffer volumes) were avoided as far as possible. The composition of the streams (MMA, alcohol, MeOH and product ester content) was determined with the aid of a gas chromatograph.

To continuously prepare n-butyl methacrylate (n-BuMA), 3.8 kg/h of MMA feed, 18 g/h of tetra-n-butyl titanate (Ti(n-OBu)$_4$) and 2.7 kg/h of n-BuOH feed were initially metered into the reaction tank. The recycle stream from the top of the low boiler distillation column also flowed continuously into the reactor (3.0 kg/h having the following composition: 0.2% by weight of n-BuMA, 31.1% by weight of n-BuOH, 66.4% by weight of MMA and 1.9% by weight of MeOH). The molar MMA:n-BuOH ratio in the reactor feed was 1.2:1. At a reactor residence time of 1 h and an MMA/MeOH azeotrope takeoff of 1.4 kg/h, a reactor temperature of 115° C. was attained. The composition of the MMA/MeOH azeotrope was 80.4% by weight of MeOH, 19.6% by weight of MMA and <5 ppm of n-BuOH. The resulting reactor effluent of 8.1 kg/h had the following composition: 63.8% by weight of n-BuMA, 11.3% by weight of n-BuOH, 24.0% by weight of MMA, 0.7% by weight of MeOH and 0.2% by weight of by-products. The n-BuOH conversion of the reactor was therefore 74%. After discharge (17) and fresh catalyst feed ceased at t=0, the n-BuOH conversion (as an indicator for the catalyst activity) was followed over a period of 24 h. As can be seen from FIG. 5, the n-BuOH conversion decreases within 24 hours surprisingly only by 18% to 56%, even though neither high-boiling secondary components are discharged nor is fresh catalyst fed, and the catalyst was recycled approx. 8 times through the overall process.

Example 3

Partial Recycling of the Catalyst (i-Butyl Methacrylate Preparation)

The reaction apparatus (1) used was a steam-heated stainless steel reaction tank having a maximum fill volume of 15 l. The reactor was connected via a vapour line to an azeotrope distillation column (2) mounted above. The azeotrope distillation column (top pressure=1 bar$_{abs}$) was a pilot plant glass column having a diameter D=0.1 m packed with Sulzer CY structured metal gauze packings of H=2 m. The feed for the reactant alcohol was disposed in the middle of the column (H=1 m). The reactor effluent was fed continuously to a low boiler distillation column (3). This distillation column was a pilot plant vacuum glass column (top pressure=120 mbar$_{abs}$) having a diameter D=0.1 m packed with Sulzer CY structured metal gauze packings of H=3.8 m. The feed was at H=2 m. The bottom was heated by means of steam. The condensed top takeoff (cycle stream) (14) was recycled continuously to the reactor. Instead of the falling-film evaporator (5) shown in FIG. 3, the continuous workup of the bottom effluent of the low boiler distillation column (15) was carried out using a thermal oil-heated glass thin-film evaporator having an evaporator surface area A=0.1 m$^2$. The vapours of this glass thin-film evaporator were passed continuously into a high boiler distillation column (4) mounted above. This was a pilot plant vacuum glass column (top pressure=150 mbar$_{abs}$) having a diameter D=0.05 m packed with Sulzer EX structured metal gauze packings of H=0.5 m. The bottom effluent was divided and partly recycled (18) continuously into the reaction tank and also partly discharged continuously from the process (17). The reactants (MMA and alcohol) were metered in continuously by means of piston metering pumps, and the catalyst (tetraalkyl titanate) was metered in dissolved in (water-free as per the specification) MMA feed. The MMA/catalyst feed was fed directly to the reactor, and the alcohol feed introduced preheated (to the internal column temperature) to the middle of the azeotrope distillation column. The continuous addition of 50-100 g/h of stabilizer solution (0.2% by weight of hydroquinone monomethyl ether in MMA or product ester) into the reflux stream of the distillation columns was effected with the aid of hose pumps. The continuous conveyance of the streams between the parts of the plant was effected either with the aid of piston metering pumps or by the sucking effect of the vacuum. Intermediate vessels (buffer volumes) were avoided as far as possible. The composition of the streams (MMA, alcohol, MeOH and product ester content) was determined with the aid of a gas chromatograph.

To continuously prepare isobutyl methacrylate (i-BuMA), 2.78 kg/h of MMA feed, 3 g/h of tetra-1-butyl titanate (Ti(i-OBu)$_4$) and 1.9 kg/h of i-BuOH feed were metered into the reaction tank. The recycle stream from the top of the low boiler distillation column also flowed continuously into the reactor (2.2 kg/h having the following composition: 2.8% by weight of i-BuMA, 39.3% by weight of i-BuOH, 56.2% by weight of MMA and 1.7% by weight of MeOH). The molar MMA:i-BuOH ratio in the reactor feed was 1.1:1. At a reactor residence time of 1.2 h and an MMA/MeOH azeotrope takeoff of 1.04 kg/h, a reactor temperature of 116° C. was attained. The composition of the MMA/MeOH azeotrope was 79% by weight of MeOH, 21% by weight of MMA and <5 ppm of i-BuOH. The resulting reactor effluent of 6.5 kg/h had the following composition: 66.8% by weight of i-BuMA, 13.1% by weight of i-BuOH, 19.0% by weight of MMA, 0.5% by weight of MeOH and 0.6% by weight of by-products. The space-time yield of the reactor based on i-BuMA was therefore 417 kg/h/m$^3$. Owing to virtually complete removal of low-boiling components relative to i-BuMA, the bottom effluent of the low boiler distillation column was a crude ester (4.25 kg/h) which already contained >99.5% by weight of i-BuMA and also all of the catalyst and the stabilizer. The yield of i-BuOH based on the overall process was therefore virtually 100%. The yield of MMA based on the overall process minus the MMA loss via the MMA/MeOH azeotrope calculated beforehand was likewise virtually 100%. At an evaporation ratio (ratio of vapour stream to feed stream) in the thin-film evaporator of about 90%, 3.81 kg/h of pure i-BuMA are finally obtained at the top of the high boiler distillation column and have the following composition: >99.9% by weight of i-BuMA, <150 ppm of i-BuOH, <10 ppm of MMA, 0 ppm of di-1-butyl ether, colour number (apha)<0.2. At 10 percent discharge (0.05 kg/h), i.e. 90% recycling (0.45 kg/h), of the bottom effluent of the thin-film evaporator, the catalyst consumption is 0.8 g of tetra-1-butyl titanate/kg of pure i-BuMA.

Compared to Example 1, the catalyst saving is therefore approx. 80%.

DESCRIPTION OF THE REFERENCE NUMERALS

1 Reaction apparatus
2 Azeotrope distillation column
3 Low boiler distillation column
4 High boiler distillation column
5 Film evaporator
6 Film evaporator
11 Methyl(meth)acrylate and catalyst feed
12 Alcohol feed
13 Methanol/methyl(meth)acrylate azeotrope
14 Low boiler cycle stream
15 Crude ester
16 Pure ester
17 High boilers and catalyst
18 Catalyst recycling

The invention claimed is:

1. A process for continuously preparing higher (meth)acrylic esters (C) in a plant comprising a reaction apparatus and a vacuum evaporation stage for receiving a bottom product remaining after separation of a highly pure ester product, the process comprising:
transesterifying methyl(meth)acrylate (A) with a higher alcohol (B) in the presence of a catalyst or catalyst mixture in the reaction apparatus;
dividing a bottom effluent from the vacuum evaporation stage into a first portion and a second portion; and
recycling the first portion to the reaction apparatus;
wherein dividing the bottom effluent from the vacuum evaporation stage comprises selecting a proportion of the bottom effluent that will constitute the first portion based on current catalyst activity.

2. A process for continuously preparing higher (meth)acrylic esters (C) in a plant comprising a reaction apparatus and a film evaporator for separating a highly pure ester product, the process comprising:
transesterifying methyl(meth)acrylate (A) with a higher alcohol (B) in the presence of a catalyst or catalyst mixture in the reaction apparatus;
dividing a bottom effluent from the film evaporator into a first portion and a second portion; and
recycling the first portion to the reaction apparatus;
wherein dividing the bottom effluent from the film evaporator comprises selecting a proportion of the bottom effluent that will constitute the first portion based on current catalyst activity.

3. A process for continuously preparing higher (meth)acrylic esters (C) in a plant comprising a reaction apparatus, a film evaporator for separating a highly pure ester product, and a vacuum evaporation stage for receiving a bottom product remaining after separation of a highly pure ester product, the process comprising:
transesterifying methyl(meth)acrylate (A) with a higher alcohol (B) in the presence of a catalyst or catalyst mixture in the reaction apparatus;
dividing a bottom effluent from the film evaporator into a first portion and a second portion;
recycling the first portion to the reaction apparatus;
dividing a bottom effluent of the vacuum evaporation stage into a third portion and a fourth portion; and
recycling the third portion to the reaction apparatus;
wherein:
dividing the bottom effluent from the film evaporator comprises selecting a proportion of the bottom effluent from the film evaporator that will constitute the first portion based on current catalyst activity; and
dividing the bottom effluent from the vacuum evaporation stage comprises selecting a proportion of the bottom effluent from the vacuum evaporation stage that will constitute the third portion based on current catalyst activity.

4. The process of claim 1, wherein the higher alcohol comprises at least one member selected from the group consisting of n-butanol, isobutanol, and 2-ethylhexanol.

5. The process of claim 1, wherein the catalyst used comprises a homogeneous catalyst.

6. The process according to claim 5, wherein the catalyst comprises a titanate of the higher alcohol (B).

7. The process according to claim 1, wherein the first portion comprises 1-95% by weight of the bottom effluent from the vacuum evaporation stage.

8. The process according to claim 7, wherein the first portion comprises 40-90% by weight of the bottom effluent from the vacuum evaporation stage.

9. The process according to claim 8, wherein the first portion comprises 60-85% by weight of the bottom effluent from the vacuum evaporation stage.

10. The process according to claim 2, wherein the first portion comprises 1-95% by weight of the bottom effluent from the film evaporator.

11. The process according to claim 10, wherein the first portion comprises 40-90% by weight of the bottom effluent from the film evaporator.

12. The process according to claim 11, wherein the first portion comprises 60-85% by weight of the bottom effluent from the film evaporator.

13. The process according to claim 3, wherein the first portion and the third portion together comprise 1-95% by weight of the bottom effluents from the film evaporator and the vacuum evaporation stage.

14. The process according to claim 13, wherein the first portion and the third portion together comprise 40-90% by weight of the bottom effluents from the film evaporator and the vacuum evaporation stage.

15. The process according to claim 14, wherein the first portion and the second portion together comprises 60-85% by weight of the bottom effluents from the film evaporator and the vacuum evaporation stage.

16. The process of claim 2, wherein the higher alcohol comprises at least one member selected from the group consisting of n-butanol, isobutanol, and 2-ethylhexanol.

17. The process of claim 3, wherein the higher alcohol comprises at least one member selected from the group consisting of n-butanol, isobutanol, and 2-ethylhexanol.

18. The process of claim 2, wherein the catalyst comprises a homogeneous catalyst.

19. The process of claim 3, wherein the catalyst comprises a homogeneous catalyst.

20. A process for continuously preparing higher (meth)acrylic esters (C) in a plant comprising a reaction apparatus and a vacuum evaporation stage for receiving a bottom product remaining after separation of a highly pure ester product, the process comprising:
transesterifying methyl(meth)acrylate (A) with a higher alcohol (B) in the presence of a catalyst or catalyst mixture in the reaction apparatus;
dividing a bottom effluent from the vacuum evaporation stage into a first portion and a second portion; and
recycling the first portion to the reaction apparatus;
wherein the first portion is recycled directly to the reaction apparatus.

* * * * *

UNITED STATES PATENT AND TRADEMARK OFFICE
CERTIFICATE OF CORRECTION

| | | |
|---|---|---|
| PATENT NO. | : 8,461,375 B2 | Page 1 of 1 |
| APPLICATION NO. | : 10/541307 | |
| DATED | : June 11, 2013 | |
| INVENTOR(S) | : Jochen Ackermann et al. | |

It is certified that error appears in the above-identified patent and that said Letters Patent is hereby corrected as shown below:

On the title page, Item (12), the 1st Inventor's Last Name is incorrect. Item (12) should read:

--(12) United States Patent
      Ackermann et al.--

On the title page, Item (75), the 1st Inventor's Last Name is incorrect. Item (75) should read:
--(75) Inventors: Jochen Ackermann, Darmstadt (DE);
              Horst Hiltner, Heppenheim (DE);
              Hermann Siegert, Seeheim-Jugenheim (DE)--

Signed and Sealed this
Thirtieth Day of July, 2013

Teresa Stanek Rea
*Acting Director of the United States Patent and Trademark Office*